US006835838B2

US 6,835,838 B2

(12) United States Patent
Chen et al.

(10) Patent No.: US 6,835,838 B2
(45) Date of Patent: Dec. 28, 2004

(54) PROCESS FOR THE MANUFACTURE OF ORGANIC COMPOUNDS

(75) Inventors: Guang-Pei Chen, Livingston, NJ (US); Prasad Koteswara Kapa, Parsippany, NJ (US); Eric M. Loeser, Lake Hiawatha, NJ (US); Ulrich Beutler, Oberwil (CH); Werner Zaugg, Riehen (CH); Michael John Girgis, Montville, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/350,615

(22) Filed: Jan. 24, 2003

(65) Prior Publication Data

US 2003/0208072 A1 Nov. 6, 2003

Related U.S. Application Data

(60) Provisional application No. 60/383,188, filed on May 24, 2002, and provisional application No. 60/352,316, filed on Jan. 28, 2002.

(51) Int. Cl.[7] ........................ C07D 215/54; C07D 407/06
(52) U.S. Cl. ..................................................... 546/173
(58) Field of Search ........................................ 546/173

(56) References Cited

U.S. PATENT DOCUMENTS

5,514,804 A     5/1996   Ohara et al. ................. 546/173

OTHER PUBLICATIONS

Soriente et al., "An Efficient Asymmetric Aldol Reaction of Chan's Diene Promoted by Chiral Ti(IV)–BINOL Complex", Tetrahedron: Asymmetry, vol. 12, pp. 959–963 (2001).
Suzuki et al., "First Systematic Chiral Syntheses of Two Pairs of Enantiomers with 3,5–Dihydroxyheptenoic Acid Chain, Associated with a Potent Synthetic Statin NK–104", Bioorganic & Medicinal Chemistry Letters, vol. 9, pp. 2977–2982 (1999).

*Primary Examiner*—Richard L. Raymond
(74) *Attorney, Agent, or Firm*—Paivi Kukkola; John D. Thallemer

(57) ABSTRACT

A method for preparing an alkali metal salt comprising: (a) condensing a disilyloxydiene with an aldehyde in the presence of a titanium (IV) catalyst in an inert solvent to form a 5(S)-hydroxy-3-ketoester; (b) reducing the 5(S)-hydroxy-3-ketoester to a 3(R),5(S)-dihydroxyester in the presence of a di(lower alkyl)methoxyborane; and (c) hydrolyzing the 3(R),5(S)-dihydroxyester in the presence of an aqueous base to form an alkali metal salt.

27 Claims, No Drawings

PROCESS FOR THE MANUFACTURE OF ORGANIC COMPOUNDS

This application claims the benefit of U.S. Provisional Application No. 60/352,316, filed Jan. 28, 2002, and U.S. Provisional Application No. 60/383,188, filed May 24, 2002 which in their entirety are herein incorporated by reference.

In one embodiment, the invention provides an enantioselective method for preparing compounds having Formula ($S_1$), ($S_2$), or ($S_3$) as follows:

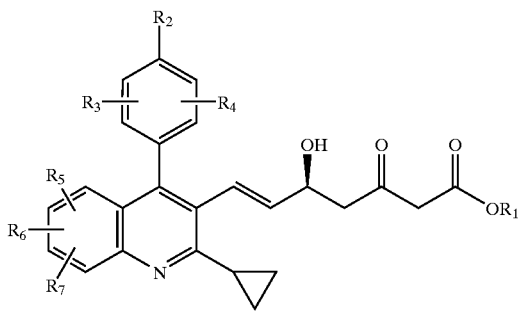

($S_1$)

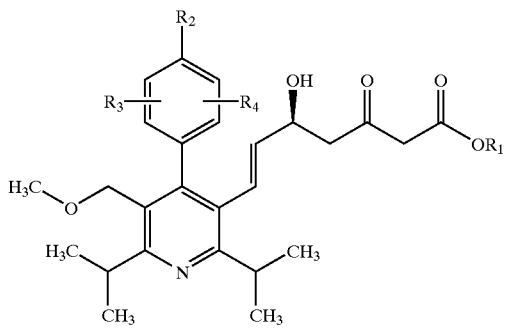

($S_2$)

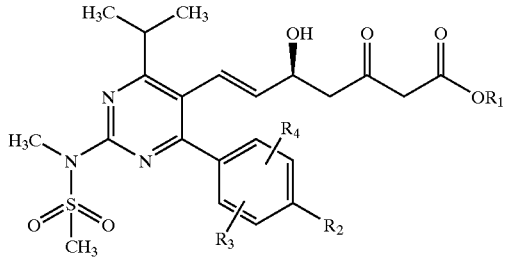

($S_3$)

wherein
$R_1$ is independently an unsubstituted or substituted alkyl, cycloalkyl or aralkyl; and
$R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy.

Listed below are definitions of various terms used to describe the compounds of the instant invention. These definitions apply to the terms as they are used throughout the specification unless they are otherwise limited in specific instances either individually or as part of a larger group.

The term "optionally substituted alkyl" refers to unsubstituted or substituted straight or branched chain hydrocarbon groups having 1–20 carbon atoms, preferably 1–7 carbon atoms. Exemplary unsubstituted alkyl groups include methyl, ethyl, propyl, isopropyl, n-butyl, t-butyl, isobutyl, pentyl, hexyl, isohexyl, heptyl, 4,4-dimethylpentyl, octyl and the like. Substituted alkyl groups include, but are not limited to, alkyl groups substituted by one or more of the following groups: halo, hydroxy, cycloalkyl, alkoxy, alkenyl, alkynyl, alkylthio, alkylthiono, sulfonyl, nitro, cyano, alkoxycarbonyl, aryl, aralkoxy, heterocyclyl including indolyl, imidazolyl, furyl, thienyl, thiazolyl, pyrrolidyl, pyridyl, pyrimidyl, piperidyl, morpholinyl and the like.

The term "lower alkyl" refers to those alkyl groups as described above having 1–7 carbon atoms, preferably 1–4 carbon atoms.

The term "halogen" or "halo" refers to fluorine, chlorine, bromine and iodine.

The term "alkenyl" refers to any of the above alkyl groups having at least two carbon atoms and further containing at least one carbon to carbon double bond at the attachment point. Groups having 2–4 carbon atoms are preferred.

The term "alkynyl" refers to any of the above alkyl groups having at least two carbon atoms and further containing at least one carbon to carbon triple bond at the attachment point. Groups having 2–4 carbon atoms are preferred.

The term "cycloalkyl" refers to optionally substituted monocyclic, bicyclic or tricyclic hydrocarbon groups of 3–12 carbon atoms, each of which may be substituted by one or more substituents, such as alkyl, halo, oxo, hydroxy, alkoxy, alkylthio, nitro, cyano, alkoxycarbonyl, sulfonyl, heterocyclyl and the like.

Exemplary monocyclic hydrocarbon groups include, but are not limited to, cyclopropyl, cyclobutyl, cyclopentyl, cyclopentenyl, cyclohexyl and cyclohexenyl and the like.

Exemplary bicyclic hydrocarbon groups include bornyl, indyl, hexahydroindyl, tetrahydronaphthyl, decahydronaphthyl, bicyclo[2.1.1]hexyl, bicyclo[2.2.1] heptyl, bicyclo[2.2.1]heptenyl, 6,6-dimethylbicyclo[3.1.1] heptyl, 2,6,6-trimethylbicyclo[3.1.1]heptyl, bicyclo[2.2.2] octyl and the like.

Exemplary tricyclic hydrocarbon groups include adamantyl and the like.

The term "alkoxy" refers to alkyl-O—.
The term "alkylthio" refers to alkyl-S—.
The term "alkylthiono" refers to alkyl-S(O)—.
The term "trialkylsilyl" refers to (alkyl)$_3$Si—.
The term "trialkylsilyloxy" refers to (alkyl)$_3$SiO—.
The term "alkylsulfonyl" refers to alkyl-S(O)$_2$—.
The term "sulfonyl" refers to alkylsulfonyl, arylsulfonyl, heteroarylsulfonyl, aralkylsulfonyl, heteroaralkylsulfonyl and the like.

The term "aryl" refers to monocyclic or bicyclic aromatic hydrocarbon groups having 6–12 carbon atoms in the ring portion, such as phenyl, naphthyl, tetrahydronaphthyl, biphenyl and diphenyl groups, each of which may optionally be substituted by 1–4 substituents, such as alkyl, halo, hydroxy, alkoxy, acyl, thiol, alkylthio, nitro, cyano, sulfonyl, heterocyclyl and the like.

The term "monocyclic aryl" refers to optionally substituted phenyl as described under aryl.

The term "aralkyl" refers to an aryl group bonded directly through an alkyl group, such as benzyl.

The term "aralkylthio" refers to aralkyl-S—.
The term "aralkoxy" refers to an aryl group bonded directly through an alkoxy group.
The term "arylsulfonyl" refers to aryl-S(O)$_2$—.
The term "arylthio" refers to aryl-S—.
The term "heterocyclyl" or "heterocyclo" refers to an optionally substituted, fully saturated or unsaturated, aromatic or nonaromatic cyclic group, for example, which is a 4- to 7-membered monocyclic, 7- to 12-membered bicyclic or 10- to 15-membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized. The heterocyclic group may be attached at a heteroatom or a carbon atom.

The term "heteroaryl" refers to an aromatic heterocycle, e.g., monocyclic or bicyclic aryl, such as pyrrolyl, pyrazolyl, imidazolyl, oxazolyl, isoxazolyl, thiazolyl, isothiazolyl, furyl, thienyl, pyridyl, pyrazinyl, pyrimidinyl, pyridazinyl, indolyl, benzothiazolyl, benzoxazolyl, benzothienyl, quinolinyl, isoquinolinyl, benzimidazolyl, benzofuryl and the like, optionally substituted by, e.g., lower alkyl, lower alkoxy or halo.

The term "heteroarylsulfonyl" refers to heteroaryl-S(O)$_2$—.

The term "heteroaralkyl" refers to a heteroaryl group bonded through an alkyl group.

Accordingly, compounds having Formula ($S_1$), ($S_2$), or ($S_3$) may be prepared by first condensing a disilyloxydiene having Formula (II)

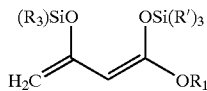

(II)

wherein
  $R_1$ is independently an unsubstituted or substituted alkyl, cycloalkyl or aralkyl; and
  R and R' represent lower alkyl, preferably ethyl or methyl, and R and R' may be identical or different,
with an aldehyde having Formula ($Q_1$), ($Q_2$), or ($Q_3$) as follows:

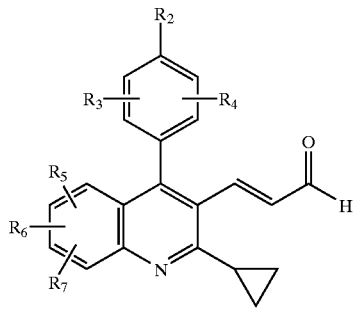

($Q_1$)

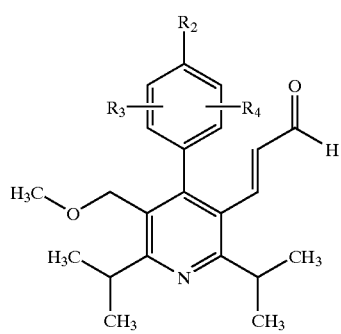

($Q_2$)

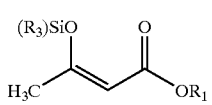

($Q_3$)

wherein $R_2$, $R_3$, $R_4$, $R_5$, $R_6$ and $R_7$ have meanings as defined for Formula ($S_1$), ($S_2$), or ($S_3$) in the presence of a titanium (IV) catalyst having Formula (IV)

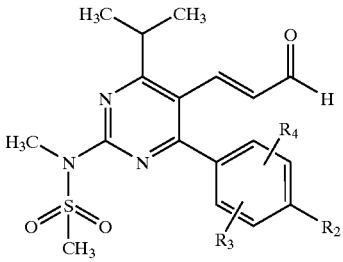

(IV)

wherein $R_8$ is a lower alkyl, and the binaphthyl moiety is in the S-configuration, in an inert solvent to obtain compounds having Formula ($S_1$), ($S_2$), or ($S_3$) in high chemical yield and enantiomeric purity.

In the aldol condensation above the molar ratio of a disilyloxydiene of Formula (II) to an aldehyde having Formula ($Q_1$), ($Q_2$), or ($Q_3$) initially present in the reaction mixture ranges from 1:1 to 6:1, preferably from 1:1 to 4:1, and more preferably from 1.5:1 to 3:1.

The disilyloxydiene of Formula (II) may be prepared by reacting an acetoacetate of Formula (VI)

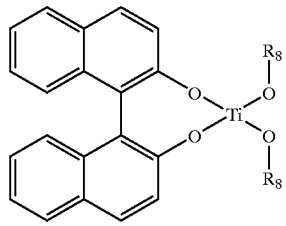

(VI)

wherein $R_1$ is independently an unsubstituted or substituted alkyl, cycloalkyl or aralkyl; with a silylating agent, such as tri(lower alkyl)silyl chloride or tri(lower alkyl)silyl trifluoromethanesulfonate, preferably trimethylsilyl chloride or triethylsilyl chloride, in the presence of a base, such as triethylamine, diisopropylethylamine or N-methylmorpholine, preferably triethylamine, in an organic solvent, such as pentane, hexane, heptane, tetrahydrofuran, diethyl ether or dichloromethane, preferably hexane, at a temperature ranging from about −25° C. to about 30° C. to form a silylenolether of Formula (VII)

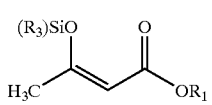

(VII)

wherein
  $R_1$ is independently an unsubstituted or substituted alkyl, cycloalkyl or aralkyl; and
  R is a lower alkyl.

The silylenolether of Formula (VII) may then be treated with a base, such as lithium diisopropylamide or lithium, sodium or potassium bis(trimethylsilyl)amide, preferably lithium diisopropylamide, followed by addition of a silylating agent, such as tri(lower alkyl)silyl chloride or tri(lower alkyl)silyl trifluoromethanesulfonate, preferably trimethylsilyl chloride or triethylsilyl chloride, in an inert solvent, such as diethylether or tetrahydrofuran, preferably tetrahydrofuran, at a temperature ranging from about −40° C. to about −100° C. to form the disilyloxydiene of Formula (II).

Lithium diisopropylamide may be generated in situ from diisopropylamine and n-butyllithium under conditions well-known in the art or as illustrated in the examples herein.

The molar ratio of the titanium (IV) catalyst of Formula (IV) to an aldehyde of Formula ($Q_1$), ($Q_2$), or ($Q_3$) initially present in the aldol condensation above ranges from 0.01:1 to 0.15:1, preferably from 0.04:1 to 0.1:1.

The titanium (IV) catalyst of Formula (IV) may be prepared in situ by reacting Ti(OR$_8$)$_4$, in which R$_8$ is lower alkyl, preferably isopropyl, with (S)-2,2′-binaphthol of the Formula (VIII)

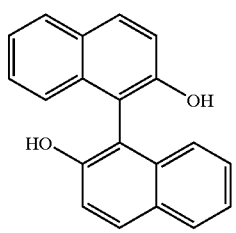

(VIII)

(S)-2,2′-Binaphthol of Formula (VIII) is commercially available, e.g., from Karlshamns under the trademark BINOL, and titanium (IV) tetra-alkoxides, preferably titanium (IV) tetraisopropoxide, may optionally be generated in situ from titanium tetrachloride and sodium or lithium alkoxide, preferably sodium or lithium isopropoxide.

The aldol condensation above may be carried out in a polar aprotic solvent, such as tetrahydrofuran, diethylether or dimethoxyethane, preferably tetrahydrofuran. A combination of solvents may also be used. The reaction temperature may range from about 0° C. to about 70° C., preferably from about 10° C. to about 60° C., and more preferably from about 15° C. to about 55° C. The reaction is conducted for a period of time from about 1 hour to about 72 hours, preferably from about 2 hours to about 24 hours.

The compounds having Formula ($S_1$), ($S_2$), or ($S_3$) may optionally be purified by physical or chemical means to enrich the enantiomeric purity. Examples of such means for enrichment include, but are not limited to, crystallization and chiral preparative chromatography, such as high pressure liquid chromatography (HPLC).

In another embodiment, the invention provides a stereoselective method for the preparation of syn-3(R),5(S)-dihydroxyesters by reducing compounds of Formula ($S_1$), ($S_2$), or ($S_3$). The syn-3(R),5(S)-dihydroxyesters have Formula ($V_1$), ($V_2$), or ($V_3$) as follows:

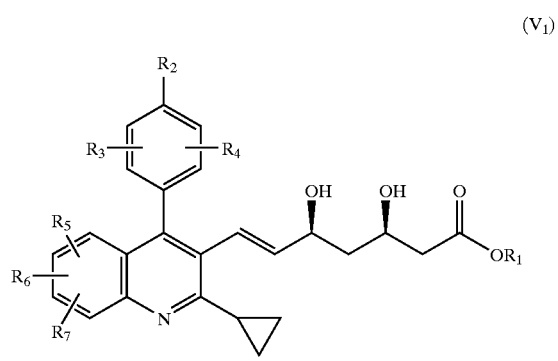

($V_1$)

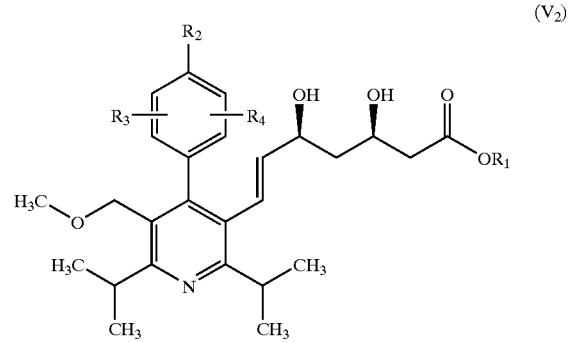

($V_2$)

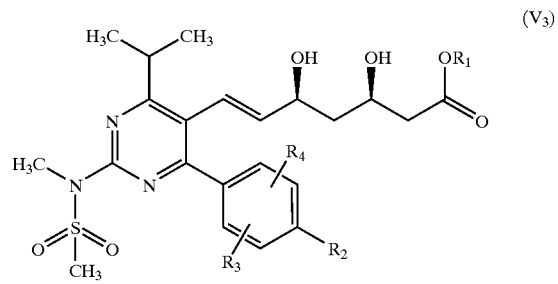

($V_3$)

wherein
$R_1$ is, independently, an unsubstituted or substituted alkyl, cycloalkyl or aralkyl; and
$R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy.

The stereoselective reduction of compounds having Formula ($S_1$), ($S_2$), or ($S_3$) may be achieved in the presence of a di(lower alkyl)methoxyborane, such as diethylmethoxyborane or dibutylmethoxyborane, preferably diethylmethoxyborane, in a polar solvent, such as tetrahydrofuran or lower alcohol, e.g., methanol or ethanol, or a mixture of solvents thereof, preferably a mixture of tetrahydrofuran and methanol. The reducing agent used in the reduction step above may be selected from a group of hydride reagents, such as sodium and lithium borohydride. Preferably the reducing agent is sodium borohydride. The reaction may be conducted at a temperature ranging from about −20° C. to about −100° C., preferably from about −50° C. to about −80° C.

In another embodiment, the invention provides methods for the preparation of calcium salts having Formula ($W_1$), ($W_2$), or ($W_3$) as follows:

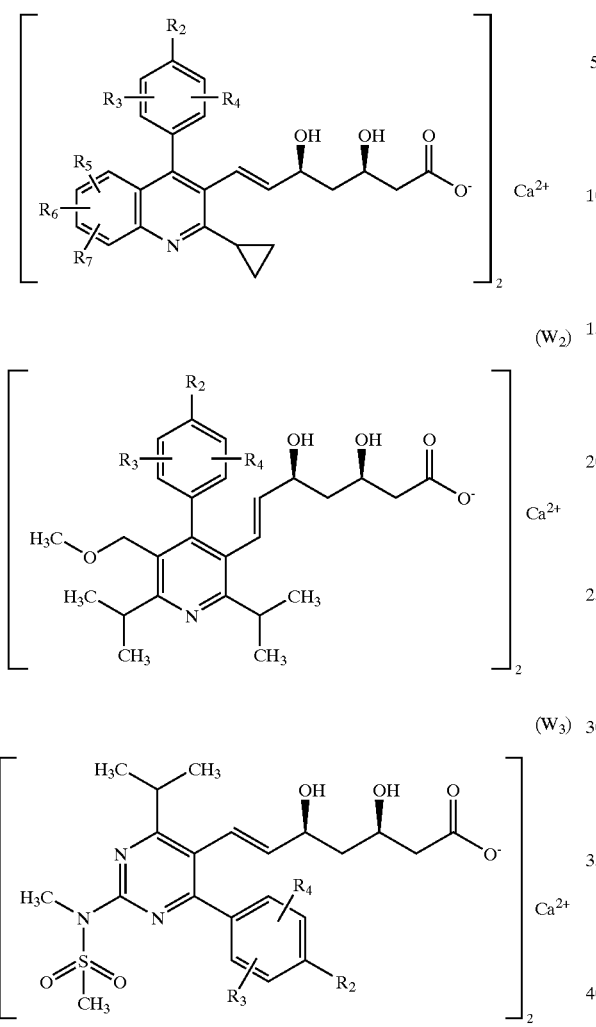

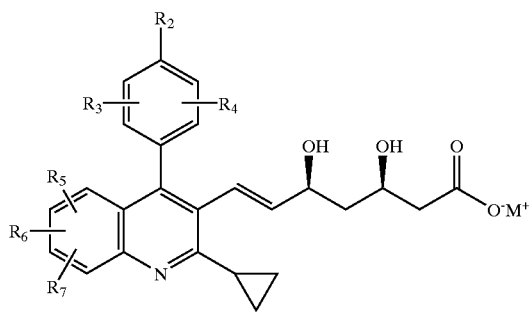

wherein $R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy.

Calcium salts of Formula ($W_1$), ($W_2$), or ($W_3$) may be prepared by first hydrolyzing compounds of Formula ($V_1$), ($V_2$), or ($V_3$) in the presence of an aqueous base to form the corresponding alkali metal salts having Formula ($X_1$), ($X_2$), or ($X_3$) as follows:

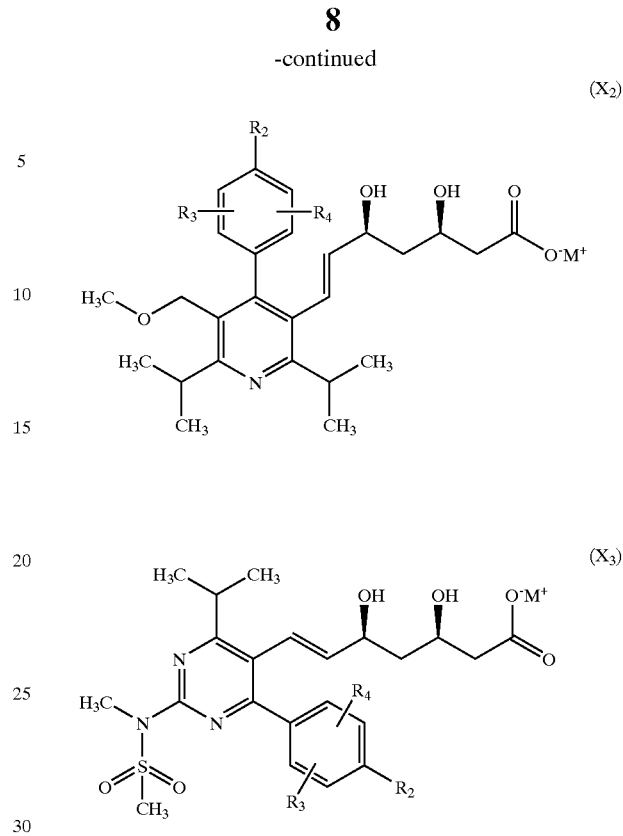

wherein $R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy; and M is sodium, lithium or potassium, preferably sodium.

The hydrolysis step above may be carried out in an organic solvent, such as a lower alcohol, preferably ethanol, and the base used in said hydrolysis is preferably selected from aqueous potassium hydroxide, aqueous lithium hydroxide and aqueous sodium hydroxide. More preferably, the base is sodium hydroxide. The hydrolysis is preferably conducted at a temperature ranging from about −10° C. to about 30° C., preferably from about 0° C. to about 25° C.

Alkali metal salts having Formula ($X_1$), ($X_2$), or ($X_3$) may then be converted to corresponding calcium salts of Formula ($W_1$), ($W_2$), or ($W_3$), by reacting an aqueous solution of an alkali metal salt of Formula ($X_1$), ($X_2$), or ($X_3$) with an aqueous solution of a suitable calcium source at an ambient temperature, preferably at room temperature. Suitable calcium sources include, but are not limited to, calcium chloride, calcium oxide and calcium hydroxide.

Alternatively, calcium salts of Formula ($W_1$), ($W_2$), or ($W_3$) may be obtained by first cyclizing compounds of Formula ($V_1$), ($V_2$), or ($V_3$) in the presence of an acid and an aprotic water-miscible solvent to form the corresponding lactone having Formula ($Y_1$), ($Y_2$), or ($Y_3$) as follows:

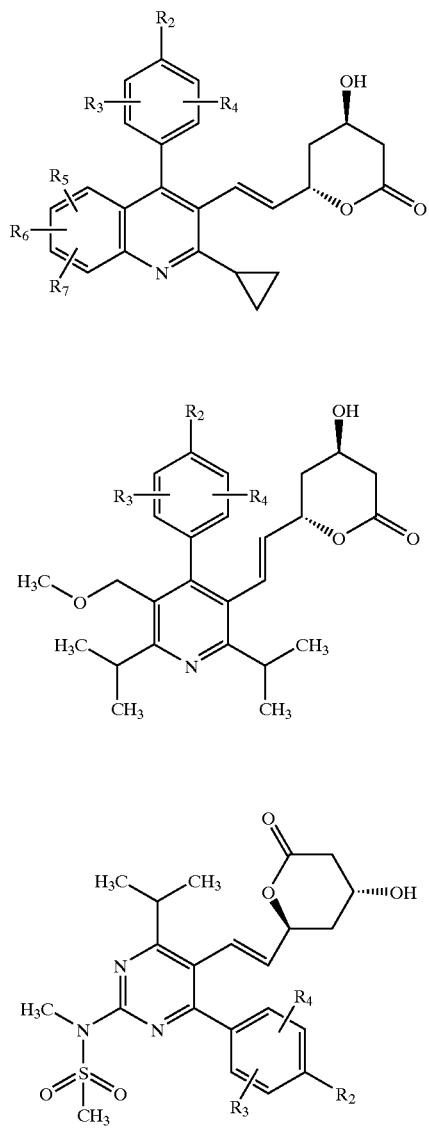

and acid addition salts thereof;

wherein $R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy.

The cyclization above may be carried out in the presence of an acid, such as trifluoroacetic acid or a strong mineral acid, preferably concentrated hydrochloric acid, in an aprotic water-miscible solvent such tetrahydrofuran or acetonitrile, preferably acetonitrile, at a temperature ranging from 0–25° C. Lactones of Formula $(Y_1)$, $(Y_2)$, or $(Y_3)$, and acid addition salts thereof, preferably hydrochloric acid salts thereof, may contain small amounts of the unreacted starting material of Formula $(V_1)$, $(V_2)$, or $(V_3)$; and the corresponding acid having Formula $(Z_1)$, $(Z_2)$, or $(Z_3)$ as follows:

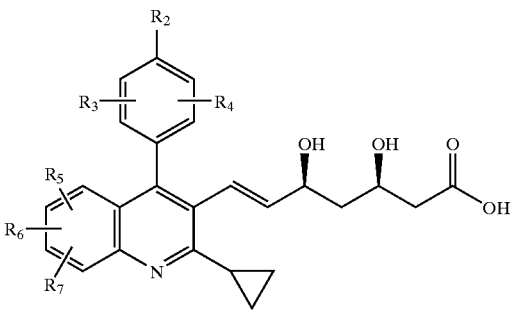

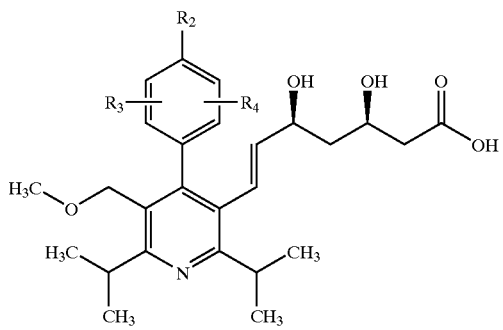

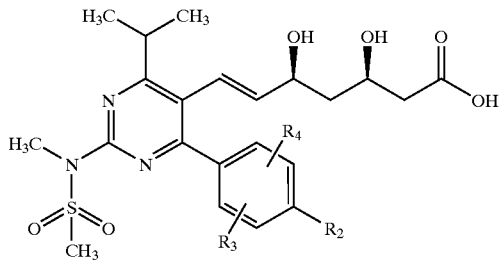

and acid addition salts thereof, preferably hydrochloric acid salts thereof;

wherein $R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy.

Lactones of Formula $(Y_1)$ $(Y_2)$, or $(Y_3)$, contaminants thereof, and acid addition salts thereof, may then be converted to the corresponding calcium salts of Formula $(W_1)$, $(W_2)$, or $(W_3)$ analogously as described herein above for compounds of Formula $(V_1)$, $(V_2)$, or $(V_3)$, or modifications thereof.

In one embodiment of the invention, the calcium salt is pitavastatin calcium.

The processes described herein above are conducted under inert atmosphere, preferably under nitrogen atmosphere. It is within the scope of the invention to use a molecular sieves during the preparation of the compounds of the invention, especially in the step of condensing a disilyloxydiene with an aldehyde of Formula $(Q_1)$, $(Q_2)$, or $(Q_3)$, in the presence of a titanium (IV) catalyst. Water may optionally be added to the molecular sieves prior to using the molecular sieves. In one embodiment, the water content of the molecular sieves is preferably from about 1 wt % to about 15 wt %.

The type of reactor used to prepare the compounds of the invention include batch, continuous, and semicontinuous reactors. It is within the scope of the invention to prepare the compounds in an external recycle reactor which allows: (i) in-situ pre-treatment or post-treatment of the solid mol sieves molecular sieves (ii) elimination of molecular sieves filtration at the end of the reaction and (iii) easy re-use of the molecular sieves for possible multicycle operation.

In starting compounds and intermediates, which are converted to the compounds of the invention in a manner described herein, functional groups present, such as amino, thiol, carboxyl and hydroxy groups, are optionally protected by conventional protecting groups that are common in preparative organic chemistry. Protected amino, thiol, carboxyl and hydroxyl groups are those that can be converted under mild conditions into free amino thiol, carboxyl and hydroxyl groups without the molecular framework being destroyed or other undesired side reactions taking place.

The purpose of introducing protecting groups is to protect the functional groups from undesired reactions with reaction components under the conditions used for carrying out a desired chemical transformation. The need and choice of protecting groups for a particular reaction is known to those skilled in the art and depends on the nature of the functional group to be protected (hydroxyl group, amino group, etc.), the structure and stability of the molecule of which the substituent is a part and the reaction conditions. Well-known protecting groups that meet these conditions and their introduction and removal are described, e.g., in McOmie, "Protective Groups in Organic Chemistry", Plenum Press, London, N.Y. (1973); and Greene, "Protective Groups in Organic Synthesis", Wiley, N.Y. (1991).

The compounds of the invention may be prepared in high enantiomeric purity, and therefor, eliminate the need for resolution. As used herein, high enantiomeric purity or enantioselectivity means at least 70% optical purity, preferably at least 80% optical purity, most preferably at least 97% optical purity.

The compounds of the invention are especially useful for treating or preventing atherosclerosis. In one embodiment of the invention, the compounds inhibit the enzyme 3-hydroxy-3-methyl-glutaryl coenzyme A (HMG-CoA) reductase which has been identified as a rate-limiting enzyme in the cholesterol biosynthetic pathway.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mmHg (=20–133 mbar). The structure of final products, intermediates and starting materials is confirmed by standard analytical methods, e.g., microanalysis, melting point (mp) and spectroscopic characteristics, e.g., MS, IR and NMR. Abbreviations used are those conventional in the art.

EXAMPLE 1

Preparation of 3-trimethylsilanyloxy-but-2-enoic Acid Ethyl Ester

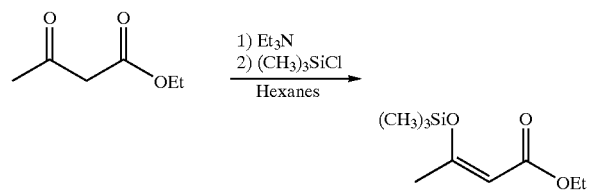

A solution of 31.9 mL (0.25 mole) of ethyl acetoacetate is stirred in hexane (350 mL) at room temperature. Triethylamine (42 mL, 0.30 mole) is added, followed by dropwise addition of trimethylsilyl chloride (35 mL, 0.276 mole) keeping the internal temperature below 25° C. using a water bath (about 18° C.). The thick white slurry is stirred overnight at room temperature. 200 mL of hexane is then added and the mixture stirred in an ice bath for 1 hour. The mixture is filtered and the solids are washed with 50 mL of cold hexane. Evaporation of the combined filtrate and washings gives 46 g of 3-trimethylsilanyloxy-but-2-enoic acid ethyl ester as a colorless, slightly cloudy oil. This material is used without further purification in the following step.

EXAMPLE 2

Preparation of 1-ethoxy-1,3-bis-trimethylsilanyloxy-buta-1,3-diene

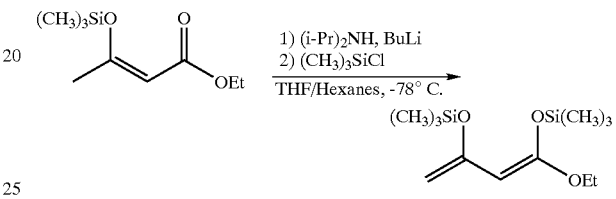

Under nitrogen atmosphere, 600 mL of anhydrous tetrahydrofuran and 38 mL of diisopropylamine (0.271 mole) is cooled to −5° C. 121 mL of 2.5 M n-butyllithium (in hexane) is added while keeping the internal temperature at −3±3° C. The mixture is then cooled to −78° C. with a dry ice acetone bath. 45.2 g (0.22 mole) of the compound of Example 1, 3-trimethylsilanyloxy-but-2-enoic acid ethyl ester is added, keeping the internal temperature below −70° C. After stirring 25 minutes, 44 mL of trimethylsilyl chloride (0.347 mole) is added while keeping the internal temperature below −70° C. The mixture is then allowed to warm up to room temperature. After evaporation of solvents, the residue is stirred in 250 mL of hexane, cooled with an ice bath and stirred for 1 hour, followed by filtration to remove solids. The filtrate is evaporated to obtain 64.7 g of 1-ethoxy-1,3-bis-trimethyl-silanyloxy-buta-1,3-diene as a yellow oil, which is used without further purification in the following step. The material is protected from moisture and stored in a freezer (−35° C.).

EXAMPLE 3

Preparation of (E)-(5S)-7-[2-cyclopropyl-4-(4-fluorophenyl)-quinolin-3-yl]-5-hydroxy-3-oxo-hept-6-enoic Acid Ethyl Ester

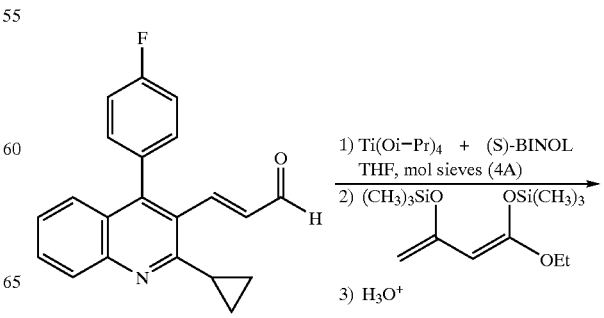

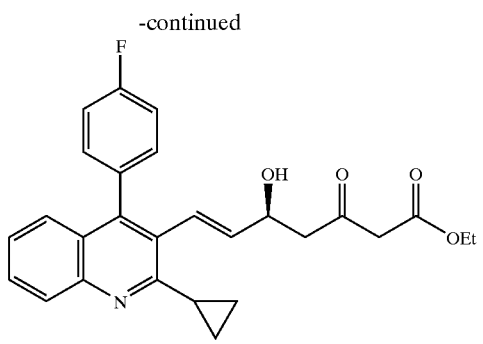

Method 1

To a dry 500 mL flask under nitrogen atmosphere are charged 25.4 g of (E)-3-[2-cyclopropyl-4-(4-fluoro-phenyl)-quinolin-3-yl]-propenal, prepared according to a process described in "Synthesis and Biological Evaluations of Quinoline-based HMG-CoA Reductase Inhibitors", *Bioorganic Med. Chem.*, Vol. 9, pp. 2727–2743 (2001), 0.080 mole, 0.91 g (S)-BINOL (4 mole %) and 5 g of molecular sieves (4A activated powder). 200 mL of anhydrous tetrahydrofuran is added and the mixture is stirred for 40 minutes 0.95 mL (4 mole %) of titanium (IV) isopropoxide is then added dropwise. The mixture becomes dark red immediately. After stirring 30 minutes at room temperature, 39.2 g (about 44 mL, 0.143 mole) of the compound of Example 2, 1-ethoxy-1,3-bis-trimethylsilanyloxy-buta-1,3-diene is added dropwise over 10 minutes. The flask is kept in a 18° C. water bath to maintain an internal temperature below 25° C. The mixture is stirred at room temperature and the disappearance of (E)-3-[2-cyclopropyl-4-(4-fluoro-phenyl)-quinolin-3-yl]-propenal is monitored by TLC (33% ethyl acetate/hexane, $R_f$ aldehyde=0.65). Reaction time varies from 1 hour to 72 hours depending on the amount of catalyst used. After the reaction is complete, 50 mL of water is added and the mixture is cooled with an ice bath, then 10 mL of 1:1 ($^v/_v$) trifluoroacetic acid/water is added. The mixture is allowed to warm to room temperature over about 30 minutes. At this time desilyation is complete as judged by TLC (disappearance of silyloxy aldol adduct $R_f$=0.75, appearance of desilylated product $R_f$=0.22). The mixture is added to a rapidly stirred flask containing 400 mL of ethyl acetate and 100 mL of saturated aqueous sodium bicarbonate. After stirring 5 minutes, the mixture is filtered to remove molecular sieves. The organic layer is separated and washed with brine, dried over anhydrous sodium sulfate and filtered. After solvent removal by evaporation, about 150 mL of hexane is added to the resulting oil over 45 minutes to induce precipitation. The mixture is stirred in an ice bath for additional 45 minutes. The precipitated solids are collected by vacuum filtration, washed with cold hexane and dried overnight under vacuum at 35° C. to form 33.8 g (94%) of (E)-(5S)-7-[2-cyclopropyl-4-(4-fluoro-phenyl)-quinolin-3yl]-5-hydroxy-3-oxo-hept-6-enoic acid ethyl ester in 97.4% optical purity (HPLC: Chiralpak AD; eluent, hexane/i-PrOH—94/6; flow rate 1 mL/min.; UV @254 nM).

Method 2

Under nitrogen a dry 1,000 mL flask is charged with 1.44 g of (S)-BINOL, 14.8 g of molecular sieves 4A powder (previously stored for at least 24 hours in an ordinary convection oven at 110° C.), and 210 mL of anhydrous tetrahydrofuran. The mixture is stirred at 20±2° C. for about 15 minutes, then 1.49 mL of titanium (IV) isopropoxide is added dropwise and the dark red mixture is warmed to 50±1° C. and stirred for 30 minutes, then cooled back to 20±2° C.

32.0 g of (2E)-3-{2-cyclopropyl-4-(4-fluorophenyl)-quinolin-3-yl}-2-propenal is added as a solid and the mixture stirred for 10 minutes. Five portions of 64.6 g (about 71 mL) of the compound of Example 2, 1-ethoxy-1,3-bis-trimethylsilanyloxy-buta-1,3-diene are then added, adding each portion over about 5 minutes (mildly exothermic) and waiting 30 minutes before adding the next portion. The internal temperature is maintained at 20±2° C. Disappearance of aldehyde is monitored by TLC (2:1 ($^v/_v$) hexane/EtOAc, $R_f$ aldehyde=0.65). When the reaction is complete, the mixture is cooled with an ice bath and 40 mL of 20% ($^v/_v$) aqueous trifluoroacetic acid is added. The mixture is warmed to room temperature. After 30 minutes, the desilylation is judged complete by TLC (disappearance of silyloxy aldol adduct $R_f$=0.75, appearance of de-silylated product $R_f$=0.22). The mixture is cooled with an ice bath and 80 g of 25% (v/v) aqueous phosphoric acid is added (exothermic) while maintaining the internal temperature below 25° C. The mixture is stirred for 3 hours, then the layers are separated. The aqueous layer is extracted with 210 mL of t-butyl methyl ether and the organic layers are combined and washed with 4×150 mL of 10% aqueous sodium chloride. Solvents are removed by rotoevaporation and the resulting oil is dissolved in 150 mL of n-butanol and evaporated under reduced pressure. This process is repeated with an additional 150 mL of n-butanol to form (E)-(5S)-7-[2-cyclopropyl-4-(4-fluoro-phenyl)-quinolin-3-yl]-5-hydroxy-3-oxo-hept-6-enoic acid ethyl ester in 99.3% optical purity (HPLC: Chiralpak AD; eluent, hexane/I-PrOH—94/6; flow rate 1 mL/min.; UV @ 254 nM). The product may be used in the next step without further purification.

It is possible to prepare molecular sieves 4A powder at other temperatures and also to add the appropriate amount of water to the THF solution of (S)-BINOL and molecular sieves (ms) in order to adjust the water content to the desired range. The effect on optical purity of these factors as well as the ratio of ms to (S)-BINOL is shown in the following table:

| ms preparation | ms:(S)-Binol ratio ($^w/_w$) | Optical Purity (%) |
|---|---|---|
| Stored in 110° C. oven >24 hours | 2.6 | 89.4 |
| Commercially Purchased Activated MS | 4.2 | 95.8 |
| Stored in 140° C. oven >24 hours | 4.2 | 97.6 |
| Stored in 110° C. oven >24 hours | 4.2 | 98.4 |
| Stored in 65° C. oven >24 hours | 4.2 | 98.4 |
| Stored in 110° C. oven >24 hours | 4.8 | 98.7 |
| Stored in 110° C. oven >24 hours | 10 | 99.0–99.6 |
| ms dried to 6.1% (w/w) water content at 125° C. under dry $N_2$ | 10 | 96.4 |
| ms dried to 8.9% (w/w) water content at 125° C. under dry $N_2$ | 10 | 98.5 |
| ms with 6.1% (w/w) $H_2O$ content and 6.1% $H_2O$ added | 10 | 98.9 |

Method 3

Under argon a dry 350-mL flask is charged with 0.92 g (S)-BINOL (5 mol %), 9.24 g relatively dry molecular sieves (4 Å activated powder; water content: 1.0%) and 130 mL of aqueous tetrahydrofuran containing 462 μL of water. This mixture is stirred at 20–25° C. for 1 hour, then 0.96 mL of titanium (IV) isopropoxide (5 mol %) is added dropwise and the dark red mixture is warmed to 50±1° C. and stirred for 30 min, then cooled back to 20±2° C. 20 g of (2E)-3-[2-cyclopropyl-4-(4-fluorphenyl)-quinolin-3-yl]-2-propenal (0.063 mol) is added as a solid and the mixture stirred for 10 min. Seven portions of 56.56 g (about 62 mL, 0.206 mol) of the compound of Example 2, 1-ethoxy-1,3-bistrimethylsilanyloxy-buta-1,3-diene are then added, adding each portion over about 5 min (mildly exothermic) and waiting 30 min before adding the next portion. The internal temperature is maintained at 20±2° C. Disappearance of aldehyde is monitored by TLC (2:1 (v/v) hexane/EtOAc, $R_f$ aldehyde=0.65). When the reaction is complete, the mixture is cooled with an ice bath and 150 g of 25% aqueous phosphoric acid is added (exothermic) within 10 min while maintaining the internal temperature below 25° C. The mixture is stirred for 1 hour at 20–25° C. The desilylation is judged complete by TLC (disappearance of silyloxy aldol adduct $R_f$=0.75, appearance of desilylated product $R_f$=0.22). Afterwards the layers are separated. The organic layer is extracted with 87 g of 25% aqueous phosphoric acid. The combined aqueous layers are extracted with 2×130 mL of t-butyl methyl ether and the organic layers are combined and washed with 4×76 mL of 10% aqueous sodium chloride. Solvents are evaporated under reduced pressure, the resulting oil is dissolved in 100 mL of n-butanol and the solution is evaporated again under reduced pressure. This process is repeated with an additional 100 mL of n-butanol to yield 49.4 g of an oily residue. 247 g of heptane fraction are added to this oil and the mixture is warmed to 45° C.±1° C. and stirred for 1 hour. After cooling to 0–5° C. the mixture is stirred for another hour at that temperature. The precipitated solids are collected by vacuum filtration, washed with 2×30 mL heptane fraction and dried overnight under vacuum at 60° C. to afford 26.3 g (89%) of (E)-(5S)-7-[2-cyclopropyl-4-(4-fluorophenyl)-quinolin-3-yl]-5-hydroxy-3-oxo-hept-6-enoic acid ethyl ester in 99.7% optical purity (HPLC: Chiralpak AD-H; eluent n-hexane/ethanol 90/10; flow rate 1.0 mL/min; T=30° C.; detection UV at 244 nm) and 95.7% chemical purity (HPLC: YMC-Pack ODS-AQ; eluent 0.01 M aqueous ammonium acetate solution/acetonitrile 45/55; flow rate 0.7 mL/min; T=60° C.; detection UV at 245 nm).

EXAMPLE 4
Preparation of (E)-(3R,5S)-7-[2-cyclopropyl-4-(4-fluoro-phenyl)-quinolin-3-yl]-3,5-dihydroxy-6-enoic Acid Ethyl Ester

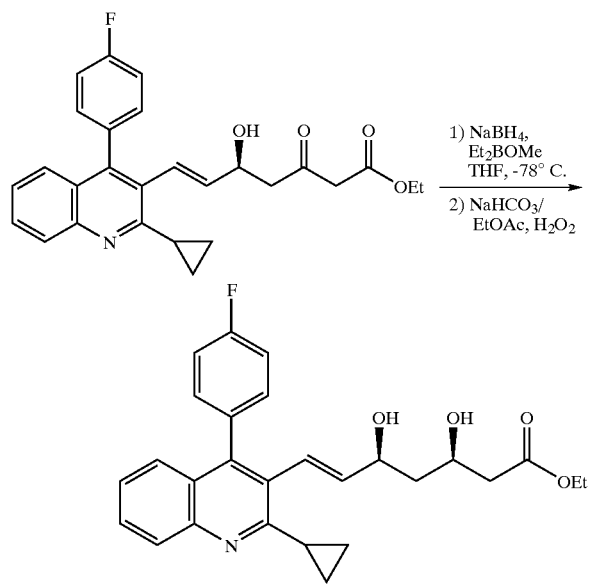

To a dry, 1 L flask in a dry ice acetone bath under nitrogen atmosphere are added 4.16 g of sodium borohydride (0.11 mole) and 300 mL of tetrahydrofuran. The mixture is stirred for about 30 minutes after internal temperature is below −70° C. 10.8 mL of diethyl-methoxyborane (0.082 mole) is added dropwise over about 10 minutes. The mixture is stirred for 15 minutes, then a solution of 30 g of the compound of Example 3, (E)-(5S)-7-[2-cyclopropyl-4-(4-fluoro-phenyl)-quinolin-3-yl]-5-hydroxy-3-oxo-hept-6-enoic acid ethyl ester (Method 1, 0.067 mole) in 60 mL of tetrahydrofuran and 100 mL of methanol is added dropwise over about 30 minutes keeping the internal temperature below −70° C. After 30 minutes, the mixture is warmed up to room temperature and added to a rapidly stirred flask containing 200 mL of saturated aqueous sodium bicarbonate and 400 mL of ethyl acetate. After mixing, the layers are separated. The organic solution is concentrated, and the residue is dissolved in 400 mL of ethyl acetate, to which is slowly added 70 mL of 30% ($^w:_w$) aqueous hydrogen peroxide, using a cooling bath to keep the internal temperature below 25° C. After stirring for 1 hour at room temperature, stirring is discontinued and the layers are separated. The organic layer is washed with 150 mL saturated sodium sulfite followed by 150 mL of brine to which 15 mL of saturated aqueous sodium bicarbonate is added. After evaporation of solvents from the organic layer, the resulting oil is distilled with toluene followed by heptane to obtain a crude oil in 97.2% optical purity (HPLC: Chiralpak AD; eluent, hexane/i-PrOH—94/6; flow rate 1 mL/min.; UV @ 254 nM). The oil is dissolved in 330 mL of 90:10 ($^v/_v$) cyclohexane/methyl-t-butyl ether at 45° C. Cooling to room temperature and stirring overnight results in the formation of a small amount of solids. By filtering off the solids the optical purity of the product remaining in the mother liquor is enriched to 99.3%. Evaporation of the mother liquor gives a thick oil which is purified by silica gel chromatography (ethyl acetate/hexanes) to form 20.8 g of (E)-(3R,5S)-7-[2-cyclopropyl-4-(4-fluoro-phenyl)-quinolin-3-yl]-3,5-dihydroxy-hept-6-enoic acid ethyl ester as a white solid in 99.3% optical purity.

EXAMPLE 5
Preparation of (E)-(3R,5S)-7-[2-cyclopropyl-4-(4-fluoro-phenyl)-quinolin-3-yl]-3,5-dihydroxy-hept-6-enoic acid calcium salt, pitavastatin calcium, Method 1

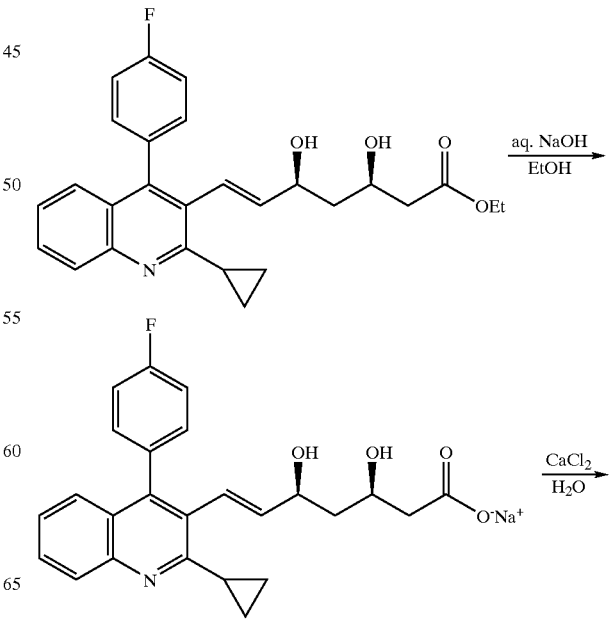

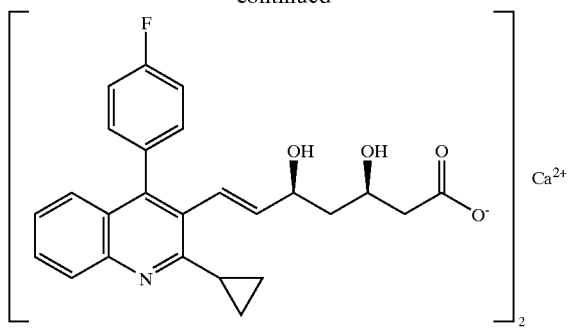

Under a nitrogen atmosphere, to a 250 mL flask are added 5.75 g (0.0128 mole) of the compound of Example 4, (E)-(3R,5S)-7-[2-cyclopropyl-4-(4-fluoro-phenyl)-quinolin-3-yl]-3,5-dihydroxy-hept-6-enoic acid ethyl ester and 40 mL of ethyl alcohol. The mixture is stirred until a clear yellow solution is formed. The solution is then cooled to an internal temperature in a range of 0–3° C., and 2.6 mL of 5 N aqueous sodium hydroxide solution (0.0128 mole) is added dropwise. The reaction is held at this temperature for 45 minutes. TLC (ethyl acetate/hexane=3:7) shows that the starting material has disappeared and the reaction is complete. The solvent is removed on a rotary evaporator at a temperature less than 45° C. 75 mL of water and 50 mL of methyl-t-butyl ether are added to the residue, and the mixture is stirred for 10 minutes, the layers are separated and the aqueous layer is washed twice with 50 mL of methyl-t-butyl ether. To completely remove organic solvent, the aqueous solution is concentrated to 20 mL with a rotary evaporator (water bath <45° C.), 50 mL of water is added to the residue, and the solution is re-distilled to 20 mL volume, and again 50 mL of water is added, then re-distilled to 20 mL under the same condition. 200 mL of water is added to the residue to form a light-yellow clear sodium salt solution. A solution of 1.035 g of calcium chloride dihydrate (0.007 mole) in 20 mL of water is added to the sodium salt solution while vigorously stirring. The solution immediately changes to a white slurry. Stirring is continued for 3 hours further. The solid is collected by filtration, washed 3 times with 50 mL of water and dried at 35° C. in a vacuum oven to obtain pitavastatin calcium in 99.4% optical purity (HPLC: Chiralpak AD; eluent, hexane/i-PrOH—94/6; flow rate 1 mL/min.; UV @ 254 nM).

EXAMPLE 6

Preparation of (E)-(3R,5S)-7-[2-cyclopropyl-4-(4-fluoro-phenyl)-quinolin-3-yl]-3,5-dihydroxy hept-6-enoic acid calcium salt, Pitavastatin calcium, Method 2

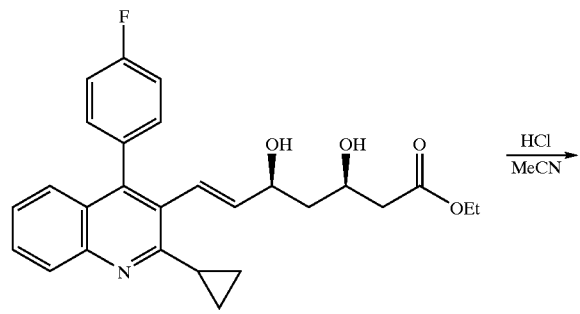

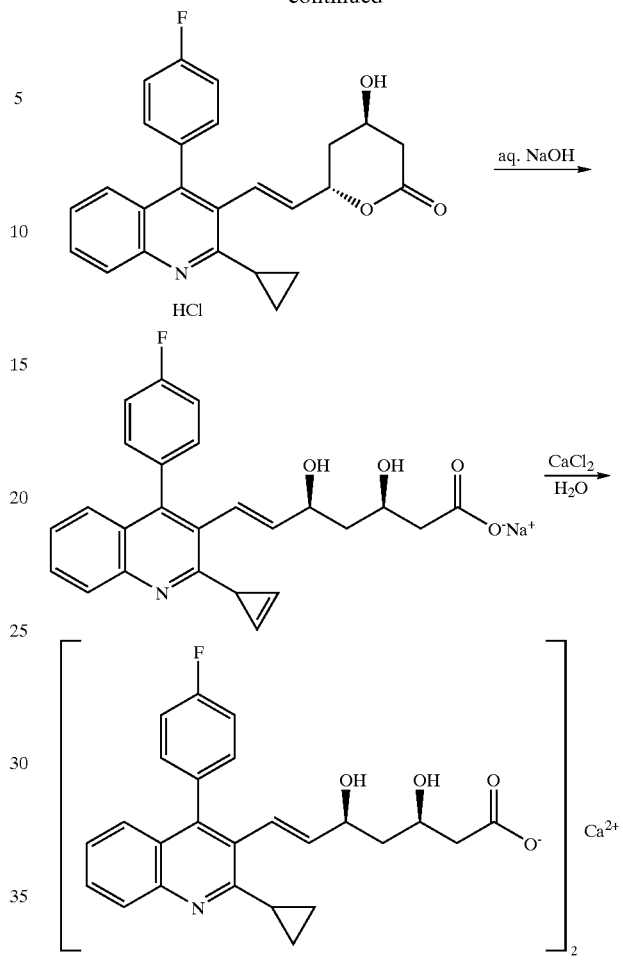

A. 6-[2-{2-Cyclopropyl-4-(4-fluorophenyl)-quinolin-3-yl}-E-ethylenyl]-tetrahyhydro-4-hydroxy-4R-trans)-2H-pyranone Hydrochloric Acid Salt A solution of the compound of Example 5, (E)-(3R,5S)-7-[2-cyclopropyl-4-(4-fluoro-phenyl)-quinolin-3-yl]-3,5-dihydroxy-hept-6-enoic acid ethyl ester (45.4 g, 0.101 mole) in 400 mL of MeCN is added to a mixture of 11.2 mL of concentrated HCl acid and 400 mL of MeCN while maintaining the reaction temperature at 20±2° C. After stirring for 3 hours further at 20±2° C., a precipitate is formed and the reaction is cooled to 0±2° C. over 1 hour. The mixture is stirred for 2 hours further at 0±2° C., and the solids are collected by vacuum filtration, washed with 100 mL of MeCN, and dried under vacuum to form 37.7 g (85%) of 6-[2-{2-cyclopropyl-4-(4-fluorophenyl)-quinolin-3-yl}-E-ethylenyl]-tetrahyhydro-4-hydroxy-4R-trans)-2H-pyranone hydrochloric acid salt.

B. (E)-(3R, 5)-7-[2-Cyclopropyl-4-(4-fluoro-phenyl)-quinolin-3-yl]-3,5-dihyroxy-hept-6-enoic Acid Calcium Salt, Pitavastatin Calcium Under a nitrogen atmosphere, 10.0 g (0.0227 mole) of 6-[2-{2-cyclopropyl-4-(4-fluorophenyl)-quinolin-3-yl}-E-ethylenyl]-tetrahyhydro-4-hydroxy-4R-trans)-2H-pyranone hydrochloric acid salt is suspended in 250 mL of water, and 9.1 mL (0.0455 mole) of aqueous 5 N sodium hydroxide is added. The mixture is stirred until dissolution is complete (about 2 hours), then filtered through celite. The filtrate is washed three times with 100 mL of methyl-t-butyl ether and the organic washings are discarded. To completely remove methyl-t-butyl ether, the aqueous solution is concentrated to about 40 mL under reduced pressure (water bath <45° C.) and readjusted to 400 mL. A solution of 1.84 g of calcium chloride dihydrate (0.0125 mole) in 20 mL of water is added to the sodium salt solution while vigorously stirring. The solution immediately changes to a white slurry. Stirring is continued to for at least 2 hours further. The solids are collected by filtration, washed with 100 mL of water and the solids are suspended in 75 mL of water and 320 mL of isopropanol. The mixture is heated at reflux until a homogeneous solution is obtained. The solution is cooled to room temperature and stirred for 18 hours. The resulting slurry is cooled to 1–3° C. and held at this temperature for 3 hours. The solids are collected by vacuum filtration, washed three times with 20 mL of water and dried at 55° C. in a vacuum oven to obtain 6.5 g (65%) of pitavastatin calcium in 99.9% optical purity (HPLC: Chiralcel OD; eluent, hexane/EtOH/TFA—900/100/0.5; flow rate 1 mL/min.; UV @ 254 nM).

EXAMPLE 7

Preparation of (E)-(3R, 5)-7-[2-cyclopropyl-4-(4-fluorophenyl)-quinolin-3-yl]-3,5-dihydroxy-hept-6-enoic Acid Calcium Salt, Pitavastatin Calcium, Method 3

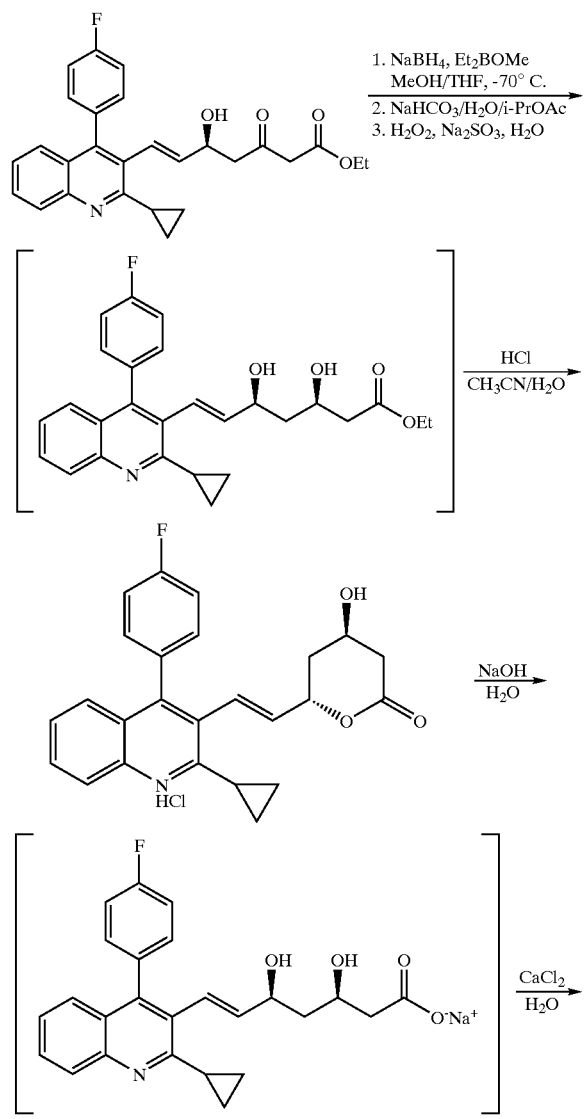

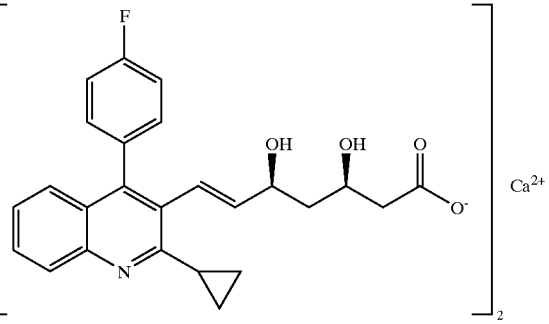

A. 6-[2-{2-cyclopropyl-4-(4-fluorophenyl)-quinolin-3-yl}-E-ethylenyl]-tetrahyhydro-4-hydroxy-4R-trans)-2H-pyran-one Hydrochloric Acid Salt In a 20 L reactor under nitrogen atmosphere dry tetrahydrofuran (2.6 L) is cooled to −68° C. and sodium borohyride (106.3 g, 2.78 mole) is added. When the internal temperature reached −75° C., diethyl methoxyborane (430 g, 2.14 mole, 50% solution in tetrahydrofuran) is added over 20 minutes followed by 140 mL of tetrahydrofuran. The white suspension is stirred for 30 minutes, then a solution of the compound produced like in Example 3, Method 3 (498.5 g, 1.07 mole) in 900 mL tetrahydrofuran and 900 mL methanol is added dropwise over 3 hours keeping the internal temperature below −70° C. The mixture is stirred for 1 hour at this temperature and then warmed up to 0° C. A sodium hydrogen carbonate solution 5% (5.3 L) is added, followed by 2 L of isopropylacetate. After vigorous stirring for 10 minutes at 20° C., stirring is discontinued and the layers are separated. The aqueous phase is re-extracted with 800 mL of isopropylacetate. After evaporation of solvents from the combined organic layer at 30–40° C., the resulting oil is dissolved in 2 L of isopropylacetate. Hydrogenperoxide 30% (263 mL, 2.5 mole) is added over 20 minutes, keeping the internal temperature at 20° C. and the mixture is stirred for 2 hours. After addition of brine (1 L) the layers are separated and the aqueous layer is re-extracted with 250 mL of isopropylacetate. To the combined organic layer, aqueous sodium sulfit (2 L, 8% solution) is added and stirred for 30 minutes until a peroxide test is negative. After separation of the layers, the organic layer is washed with 1 L of water and evaporated to dryness at 30–40° C. under vacuum. The resulting oil is dissolved in 3.2 L of acetonitrile, evaporated to dryness, re-dissolved in 2 L of acetonitril and filtered through celite. This solution is added over 20 minutes to a mixture of 37% hydrochloric acid (142 g, 1.44 mole) in 3 L acetonitrile. After seeding the mixture is stirred for 3 hours at 20° C. and over night at 0–5° C. The solid is filtered off, washed with 840 mL cold acetonitrile and dried at 35° C. in a vacuum oven to afford 389 g (82%) of 6-[2-{2-cyclopropyl-4-(4-fluorophenyl)-quinolin-3-yl}-E-ethylenyl]-tetrahyhydro-4-hydroxy-4R-trans)-2H-pyranone hydrochloric acid salt as a pale orange powder.

B. (E)-(3R, 5)-7-[2-cyclopropyl-4-(4-fluoro-phenyl)-quinolin-3-yl]-3,5-dihydroxy-hept-6-enoic Acid Calcium Salt, Pitavastatin Calcium Under a nitrogen atmosphere, 388 g (0.873 mole) of the 6-[2-{2-cyclopropyl-4-(4-fluorophenyl)-quinolin-3-yl}-E-ethylenyl]-tetrahyhydro-4-hydroxy-4R-trans)-2H-pyranone hydrochloric acid salt is suspended in 9.6 L of water, and 349 mL (1.746 mole) of aqueous 5 N sodium hydroxide is added. The mixture is stirred for 2 hours, then filtered through celite and washed with 2 L of water. The filtrate is washed three times with 3.8 L (=11.4 L) of ethylacetate and the organic washings are discarded. To completely remove ethylacetate, the aqueous solution is concentrated to about 11 L under reduced pressure at 35–40° C. A solution of 70.61 g of calcium chloride dihydrate (0.480 mole) in 786 mL of water is added to the sodium salt solution while vigorously stirring. The solution immediately changes to a white slurry. Stirring is continued to for at least 2 hours further. The solids are collected by filtration, washed with 2 L of water and dried at 40° C./20 mbar for 24 hours to obtain pitavastatin calcium (358.5 g, 93%, purity 99 area-% HPLC); diastereomeric purity 98.9% (HPLC: YMC-Pack Pro C18; eluent 0.01 M aqueous sodium chloride solution, acetic acid, pH 3.4/methanol; flow rate 0.6 mL/min.; T=40° C.; detection UV at 245 nM); optical purity: 99.7% (HPLC: Chiralcel OD; eluent, hexane/EtOH/TFA—900/100/0.5; flow rate 1 mL/min.; UV @254 nM). This product can be re-crystallized as in Example 6B to obtain a diastereomeric purity of 99.8% and an optical purity of >99.9%.

EXAMPLE 8

Seven disilyloxydiene reagents with different $R_1$ groups have been evaluated for enantioselectivity in the aldol condensation according to the procedure set forth in Method 1 of Example 3 to form 5(S)-hydroxy-3-ketoesters as follows:

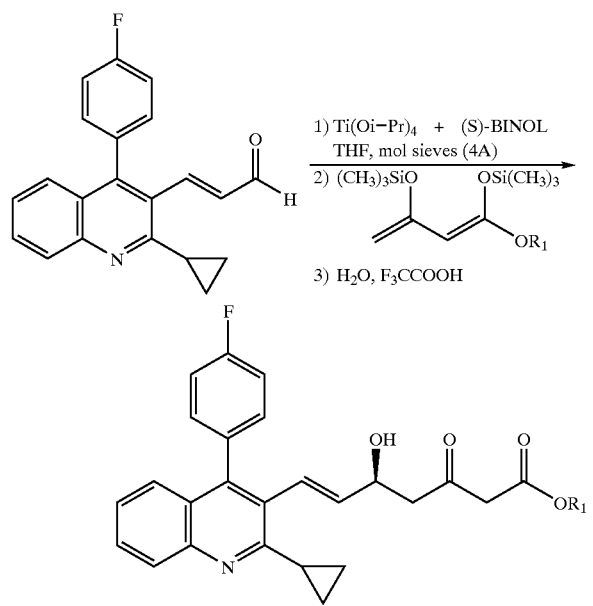

The results are summarized in following table, and show that greater enantiomeric purity is achieved when $R_1$ is a linear alkyl group, such as methyl, ethyl or n-propyl, as compared to a branched alkyl group, such as isopropyl or isobutyl:

| $R_1$ | Yield[1] (%) | Optical purity[2] (%) | mp (° C.) |
|---|---|---|---|
| Me | 62 | 98 | 47–51 |
| Et | 91[3] | 97[3] | 81–84 |
| n-Pr | 91 | 98 | Oil |
| i-Pr | 74[3] | 83[3] | 82–83 |
| MeO(CH$_2$)$_2$— | 90 | 90 | Oil |
| i-Bu | 71 | 80 | Oil |
| Benzyl | 47 | 88 | Oil |

[1]Isolated yields.
[2]Determined by HPLC.
[3]Average of two experiments.

EXAMPLE 9

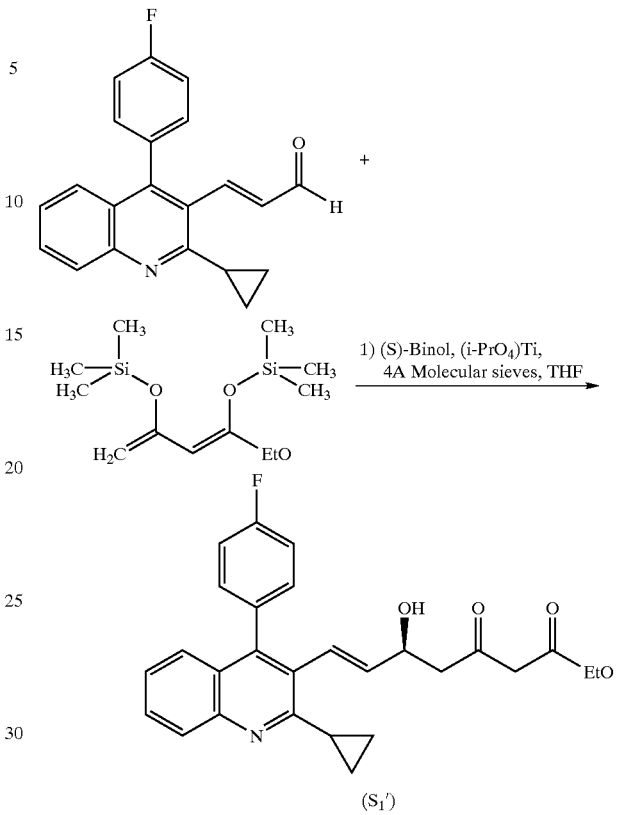

5(S)-hydroxy-3-ketoester ($S_1'$) was prepared using an external recycle reactor. The reactor contained a 0.5-L jacketed vessel equipped with a retreat-curve impeller and temperature sensor to determine the batch temperature; a recycle pump; a 1"-OD tube packed with solids; two three-way valves placed, respectively, at the inlet and exit of the tube; connecting tubing to form an external recycle loop; and a dosing pump for adding liquid to the recycle loop The 1"-OD tube was packed with 5.06 g of 4A mol sieve pellets (Aldrich, Cat. No. 334304, Batch No.07701 LS) having a diameter of 1.6-mm. The 4A mol sieves were confined to the middle part the 1"-tube using metal mesh screens. The top and bottom of the tube were packed with 3-mm Pyrex glass beads. The sieves were heated to 115° C. under a flow of $N_2$ (100 cm$^3$/min) and kept at this temperature for 12.5 h. Heating was accomplished using an electrical heating tape wrapped around the tube. The temperature of the bed of solids was determined using a movable RTD placed inside a ⅛" tube mounted co-axially inside the 1" tube. The two three-way valves were than switched to allow flow into the tube from the vessel, and out of the tube back to the vessel.

The vessel was purged of air with nitrogen, and charged with:0.4788 g of (S)-Binol, 10.70 g of aldehyde, and 222.03 g of tetrahydrofuran, and sealed. The agitator was turned on at 250 rpm, and the vessel headspace was purged of air. Flow to the recycle loop was started by turning on the recycle pump (recycle flow rate=825 cm$^3$/min) and the agitation rate was reduced to 225 rpm. The batch temperature was controlled at 19° C.

After about 30 min, 45.44 g of a solution (comprised of 1.00 g of titanium (IV) isopropoxide in 88.95 g of THF) was added using the dosing pump over 6 min. About 20-min after this addition, 4.31 g of disilyloxydiene were added over 6 min. After 1 h, a second portion of disilyloxydiene (8.9 g over 2 min) was added. After 1 h, a third portion of disilyloxydiene (8.8 g over 2 min) was added. After 2 days, the aldehyde disappearance was complete based on TLC analysis. The vessel and recycle loop were emptied and the reaction mixture was worked up in a separate flask by adding slowly 25 mL of 20% (v/v) aqueous trifluoroacetic acid keeping the internal temperature below 10° C. (ice bath cooling). The mixture was then warmed to room temperature and stirred for 30 minutes. TLC showed conversion of the initial trimethylsilyl adduct to ($S_1'$) was complete. 300 mL of t-BuOMe and 200 mL of saturated $NaHCO_3$ were added and the mixture was stirred thoroughly. After filtering the mixture to remove a small amount of insolubles, the layers were separated and the organic layer was rotoevaporated to obtain an oil which was distilled with n-BuOH (2×160 mL, 45° C. bath temp, about 20 mbar) to remove ethyl acetoacetate (formed by hydrolysis of the excess disilyloxydiene during workup). Based on NMR analysis of the crude product, an ($S_1'$) yield of 81.6% was obtained, and the amount of undesired enantiomer was below the limit of detection.

EXAMPLE 10

The vessel recycle loop used in Example 9 was rinsed three times, each time with at least 250 mL of tetrahydrofuran, and subsequently dried by flowing nitrogen at room temperature. The dry vessel was charged with: 0.48 g of (S)-binol, 10.67 g of aldehyde, and 222 g of tetrahydrofuran. The loop and vessel were purged of air with nitrogen. The agitator was turned on, and recycle flow was started at the same flow rate as in Example 9, with the batch temperature controlled at 19° C.

After 20 min, 44.96 g of a solution of titanium (IV) isopropoxide (prepared by adding 1 g of the latter to 89.10 g of THF) was added over 4 min. After 30 min, 4.4 g of disilyloxydiene were added over 10 min. A second portion of disilyloxydiene was added (8.6 g over 2 min) one hour later. A third disilyloxydiene portion (8.8 g over 2 min) was added after 1 hour. After 2 days, the reaction was stopped and the reaction mixture was worked up as in Example 9. The yield of ($S_1'$), based on NMR analysis of the crude, was 90%, and the amount of undesired enantiomer was below the limit of detection.

While the invention has been described with particular reference to certain embodiments thereof, it will be understood that changes and modifications may be made by those of ordinary skill within the scope and spirit of the following claims:

What is claimed is:
1. A method for preparing a compound having Formula ($S_1$) as follows

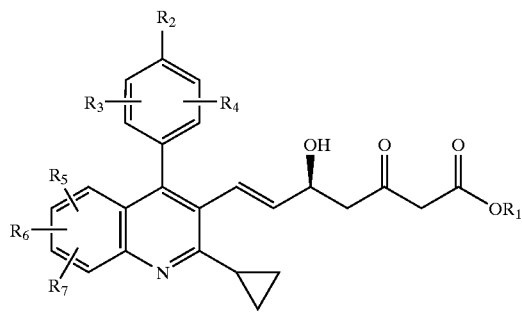

said method comprising condensing a disilyloxydiene of Formula (II)

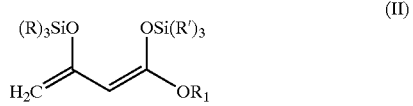

with an aldehyde having Formula ($Q_1$) as follows

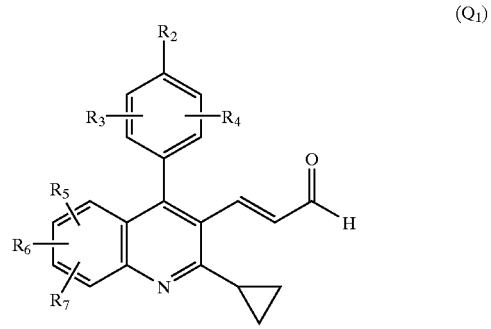

in the presence of a titanium (IV) catalyst having Formula (IV)

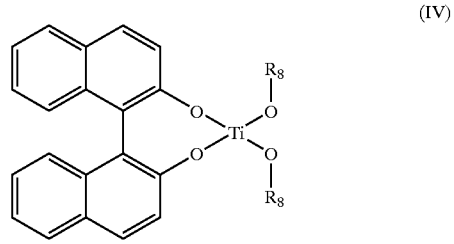

in an inert solvent to obtain a 5(S)-hydroxy-3-ketoester having Formula ($S_1$),
wherein
$R_1$ is optionally substituted alkyl, cycloalkyl or aralkyl;
$R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy;
$R_8$ is a lower alkyl; the binaphthyl moiety is in the S-configuration; and
R and $R^1$ are, independently, a lower alkyl.

2. A method according to claim 1, wherein the molar ratio of a disilyloxydiene of Formula (II) to an aldehyde of Formula ($Q_1$) initially present in the reaction mixture ranges from 1:1 to 6:1.

3. A method according to claim 1, wherein the method additionally comprises using molecular sieves.

4. A method according to claim 3, wherein water is added to the molecular sieves prior to using the molecular sieves.

5. A method according to claim 4, wherein the water content of the molecular sieves is from 1 wt % to 15 wt %.

6. A method according to claim 5, wherein the water content of the molecular sieves is from 2.6 wt % to 10 wt %.

7. A method according to claim 5, wherein the molecular sieves are situated in a fixed bed external to a reaction vessel, and the reaction mixture is passed through the fixed bed.

8. A method according to claim 7, wherein the molecular sieves are reused.

9. A method according to claim 1, wherein the disilyloxydiene of Formula (II) is prepared by (a) reacting an acetoacetate of Formula (VI)

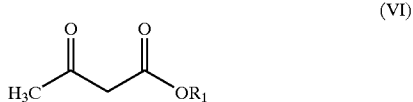
(VI)

with a silylating agent in the presence of a base and an organic solvent to form a silylenolether having Formula (VII)

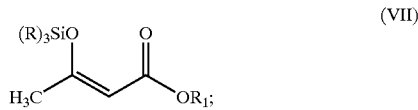
(VII)

(b) treating the silylenolether having Formula (VII) with a base and a silylating agent in an inert solvent to form a disilyloxydiene of Formula (II), wherein $R_1$ is, independently, an unsubstituted or substituted alkyl, cycloalkyl or aralkyl; and R is a lower alkyl.

10. A method according to claim 9, wherein the organic solvent in step (a) is hexane, and the inert solvent in step (b) is diethylether or tetrahydrofuran.

11. A method according to claim 9, wherein the base in step (a) is triethylamine.

12. A method according to claim 9, wherein the base in step (b) is selected from the group consisting of lithium diisopropylamide, lithium bis(trimethylsilyl)amide, sodium bis(trimethylsilyl)amide, and potassium bis(trimethylsilyl) amide.

13. A method according to claim 9, wherein the silylating agent in steps (a) and (b) is trimethylsilyl chloride.

14. A method according to claim 1, wherein the titanium (IV) catalyst of Formula (IV) is prepared in situ by reacting titanium (IV) tetraisopropoxide with (S)-2,2'-binaphthol of Formula (VIII)

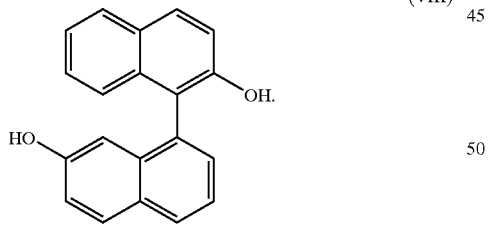
(VIII)

15. A method according to claim 14, wherein the molar ratio of the titanium (IV) catalyst of Formula (IV) to an aldehyde of Formula ($Q_1$) initially present in the reaction mixture ranges from 0.01:1 to 0.15:1.

16. A method according to claim 1, wherein $R_1$ is lower alkyl, $R_2$ is halogen; and $R_3$, $R_4$, $R_5$, $R_6$ and $R_7$ are hydrogen.

17. A method according to claim 16, wherein $R_1$ is ethyl; and $R_2$ is fluorine.

18. A method according to claim 1, which method further comprises reducing a 5(S)-hydroxy-3-ketoester having Formula ($S_1$) in the presence of a di(lower alkyl) methoxyborane, a reducing agent and a polar solvent to afford a 3(R),5(S)-dihydroxyester of Formula ($V_1$)

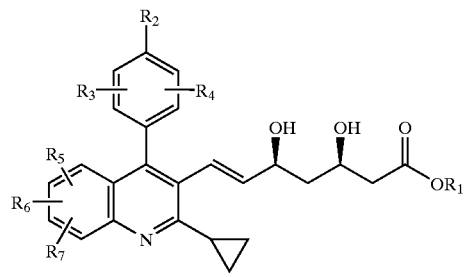
($V_1$)

wherein $R_1$ is optionally substituted alkyl, cycloalkyl or aralkyl; and $R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy.

19. A method according to claim 18, wherein the di(lower alkyl)methoxyborane is diethylmethoxyborane or dibutylmethoxyborane.

20. A method according to claim 18, wherein the polar solvent is selected from the group consisting of tetrahydrofuran, methanol, ethanol, isopropanol, butanol, and mixtures thereof.

21. A method according to claim 18, wherein the reducing agent is sodium borohydride or lithium borohydride.

22. A method according to claim 1, which method further comprises (a) reducing a 5(S)-hydroxy-3-ketoester having Formula ($S_1$) in the presence of a di(lower alkyl)methoxyborane, a reducing agent and a polar solvent to afford a 3(R), 5(S)-dihydroxyester of Formula ($V_1$)

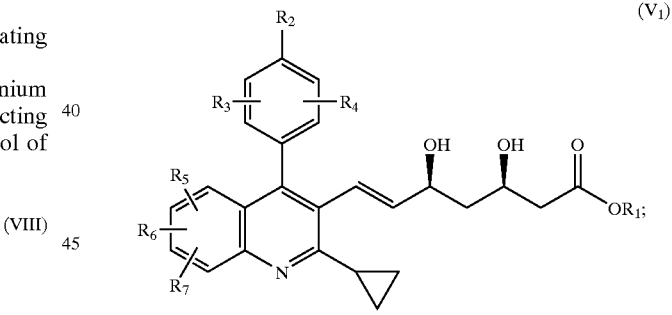
($V_1$)

(b) hydrolyzing a 3(R),5(S)-dihydroxyester having Formula ($V_1$) in the presence of an aqueous base to form an alkali metal salt having Formula ($X_1$) as follows

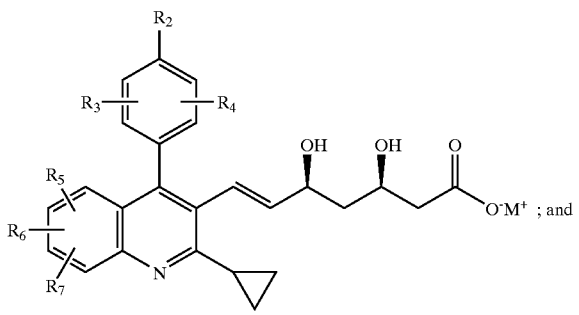
($X_1$)

; and (c) converting an alkali metal salt of Formula ($X_1$) to a calcium salt of Formula ($W_1$)

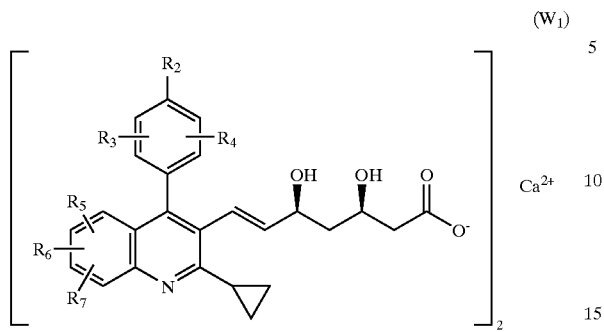

in the presence of a calcium source,
wherein
$R_1$ is optionally substituted alkyl, cycloalkyl or aralkyl;
$R_2$, $R_3$, $R_4$, $R_5$, $R_6$ and $R_7$ are, independently, hydrogen, halogen, hydroxy, optionally substituted alkyl, cycloalkyl, aralkyl, heterocyclyl, heteroaralkyl, optionally substituted alkoxy, aryloxy, aralkoxy, heterocyclooxy or heteroaralkoxy; and
M is sodium, lithium or potassium.

23. A method according to claim 22, wherein the calcium source in step (c) is calcium chloride.

24. A method according to claim 1, which method further comprises
(a) reducing a 5(S)-hydroxy-3-ketoester having Formula ($S_1$) in the presence of a di(lower alkyl)methoxyborane, a reducing agent and a polar solvent to afford a 3(R), 5(S)-dihydroxyester of Formula ($V_1$)

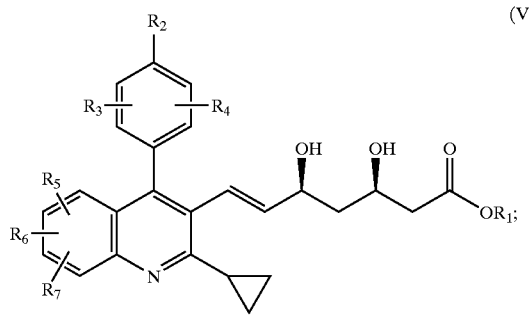

(b) cyclizing a 3(R),5(S)-dihydroxyester having Formula ($V_1$) in the presence of an acid and an aprotic water-miscible solvent to form a lactone having Formula ($Y_1$) as follows

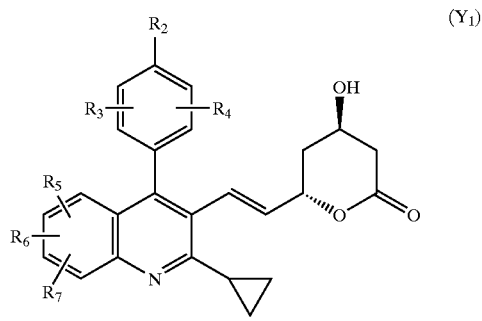

and acid addition salts thereof;
(c) hydrolyzing a lactone having Formula ($Y_1$), or acid addition salts thereof, in the presence of an aqueous base to form an alkali metal salt having Formula ($X_1$) as follows

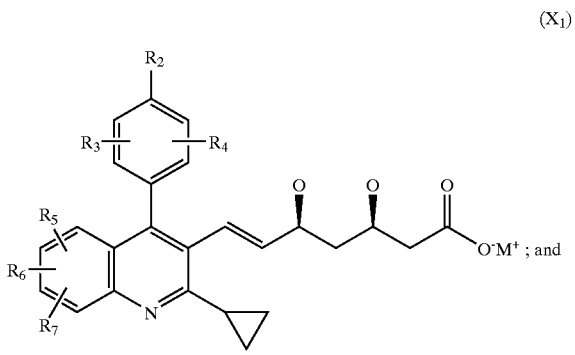

(d) converting an alkali metal salt of Formula ($X_1$) to a calcium salt of Formula ($W_1$)

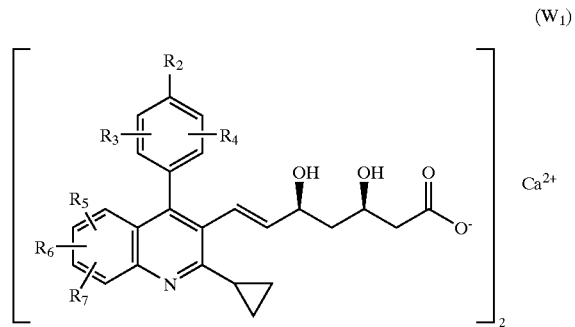

in the presence of a calcium source,
wherein
$R_1$ is optionally substituted alkyl, cycloalkyl or aralkyl;
$R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy; and
M is sodium, lithium or potassium.

25. A method according to claim 24, wherein the acid in step (b) is concentrated hydrochloric acid, the aprotic water-miscible solvent is acetonitrile, and the acid addition salt thereof is the hydrochloric acid salt.

26. A method according to claim 1, which method further comprises
(a) reducing a 5(S)-hydroxy-3-ketoester having Formula ($S_1$) in the presence of a di(lower alkyl)methoxyborane, a reducing agent, and a polar solvent to afford a 3(R),5(S)-dihydroxyester having Formula ($V_1$) as follows

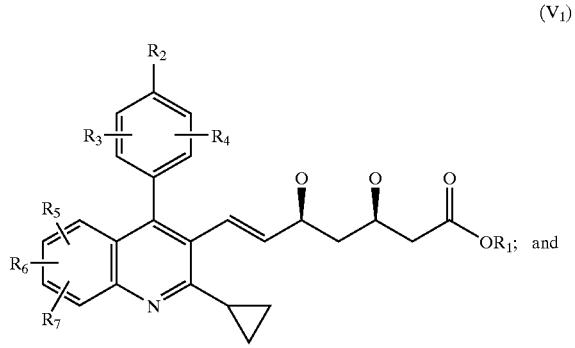

(b) hydrolyzing a 3(R),5(S)-dihydroxyester having Formula ($V_1$) in the presence of an aqueous base to form an alkali metal salt having Formula ($X_1$)

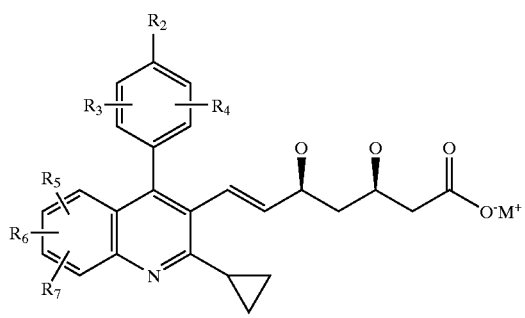

($X_1$)

wherein $R_1$ is optionally substituted alkyl, cycloalkyl or aralkyl;

$R_2$, $R_3$, $R_4$, $R_5$, $R_6$ and $R_7$ are, independently, hydrogen, halogen, hydroxy, optionally substituted alkyl, cycloalkyl, aryl, aralkyl, heterocyclyl, heteroaralkyl, optionally substituted alkoxy, aryloxy, aralkoxy, heterocyclooxy or heteroaralkoxy; and M is sodium, lithium or potassium.

27. A method according to claim 26, wherein the aqueous base in step (b) is sodium hydroxide and M represents sodium.

* * * * *